United States Patent
Smith et al.

(10) Patent No.: US 9,399,782 B2
(45) Date of Patent: Jul. 26, 2016

(54) METHODS FOR PRODUCING FERMENTATION PRODUCTS

(75) Inventors: Mads Torry Smith, Raleigh, NC (US); Guillermo Coward-Kelly, Wake Forest, NC (US); Dan Nilsson, Raleigh, NC (US); Zhengfang Kang, Raleigh, NC (US); Prashant Iyer, Raleigh, NC (US); Randy Deinhammer, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 865 days.

(21) Appl. No.: 12/666,919

(22) PCT Filed: Jun. 27, 2008

(86) PCT No.: PCT/US2008/068575
§ 371 (c)(1),
(2), (4) Date: Mar. 16, 2010

(87) PCT Pub. No.: WO2009/003167
PCT Pub. Date: Dec. 31, 2008

(65) Prior Publication Data
US 2010/0196980 A1 Aug. 5, 2010

Related U.S. Application Data

(60) Provisional application No. 60/946,521, filed on Jun. 27, 2007, provisional application No. 60/952,685, filed on Jul. 30, 2007.

(51) Int. Cl.
*C12P 7/10* (2006.01)
*C12P 19/14* (2006.01)

(52) U.S. Cl.
CPC . *C12P 7/10* (2013.01); *C12P 19/14* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 7,754,456 B2 * | 7/2010 | Penttila et al. | 435/165 |
| 8,227,221 B2 * | 7/2012 | Soong et al. | 435/161 |
| 2007/0031919 A1 | 2/2007 | Dunson | |
| 2007/0077630 A1 | 4/2007 | Harris et al. | |
| 2007/0141660 A1 | 6/2007 | Chotani | |

FOREIGN PATENT DOCUMENTS

| | | |
|---|---|---|
| CN | 1880416 | 12/2006 |
| CN | 1912129 | 2/2007 |
| WO | 91/10740 A1 | 7/1991 |
| WO | 2005/040392 A1 | 5/2005 |
| WO | 2005/074656 A2 | 8/2005 |
| WO | 2006/101832 A2 | 9/2006 |
| WO | 2007/089677 A2 | 8/2007 |
| WO | 2008/065433 A1 | 6/2008 |

OTHER PUBLICATIONS

Sedlak and Ho, "Production of Ethanol from Cellulosic Biomass Hydrolysates Using Genetically Engineered *Saccharomyces* Yeast Capable of Cofermenting Glucose and Xylose", Applied Biochemistry and Biotechnology, vol. 114 pp. 403-416, (2004).*
Petersson and Liden, "Fed-batch cultivation of *Saccharomyces cerevisiae* on lignocellulosic hydrolyzate", Biotechnol. Lett. 29: 219-225 (2007); Published online Nov. 8, 2006.*
Purwadi et al., International Journal of Molecular Sciences, vol. 8, pp. 920-932 (2007).
Zhang et al., Niang Jiu, vol. 4, pp. 76-77 (2000).
International Search Report issued in corresponding international application No. PCT/US2008/068575 dated Sep. 23, 2008.
Agbogbo et al., Applied Biochemistry and Biotechnology, vol. 136-140, pp. 653-662 (2007).
Agbogbo et al., Applied Biochemistry and Biotechnology, vol. 145, pp. 53-58 (2007).
Chung et al., Biotechnology and Bioengineering, vol. 27, No. 3, pp. 308-315 (1985).
Kida et al., Journal of Fermentation and Bioengineering, vol. 69, No. 1, pp. 39-45 (1990).
Roca et al., Appl. Microbiol. Biotechnol., vol. 60, pp. 560-563 (2003).
Parajo et al., Biotechnology Letters, vol. 18, No. 5, pp. 593-598 (1996).
Ohgren et al., Journal of Biotechnology, vol. 126, pp. 488-498 (2006).
Haddad et al, Appl Microbiol, vol. 1, pp. 153-156 (1953).

* cited by examiner

*Primary Examiner* — Anand Desai
(74) *Attorney, Agent, or Firm* — Kelly Reynolds

(57) ABSTRACT

The invention relates to methods for producing a fermentation product from a lignocellulose-containing material comprising i) pre-treating lignocellulose-containing material; ii) hydrolyzing pre-treated lignocellulose-containing material; iii) fermenting using a fermenting organism; wherein fermentation is initiated and carried out at: a) a fermentation organism cell count in the range from $10\text{-}250 \times 10^{10}$ cells per L fermentation medium; or b) a fermentation organism concentration in the range from 2-90 g dry weight fermenting organism per L fermentation medium.

19 Claims, 7 Drawing Sheets

METHODS FOR PRODUCING FERMENTATION PRODUCTS

CROSS-REFERENCE TO RELATED APPLICATIONS

This application is a 35 U.S.C. 371 national application of PCT/US2008/068575 filed Jun. 27, 2008, which claims priority or the benefit under 35 U.S.C. 119 of U.S. provisional application Nos. 60/946,521 filed on Jun. 27, 2007 and 60/952,685 filed Jul. 30, 2007, the contents of which are fully incorporated herein by reference.

TECHNICAL FIELD

The present invention relates to methods for producing fermentation products from lignocellulose-containing material using one or more fermenting organisms.

BACKGROUND OF THE INVENTION

Due to the limited reserves of fossil fuels and worries about emission of greenhouse gases there is an increasing focus on using renewable energy sources.

Production of fermentation products from lignocellulose-containing material is known in the art and includes pre-treating, hydrolyzing, and fermenting the lignocellulose-containing material.

The fermentation step is carded out using a fermenting organism capable of converting fermentable sugars into the desired fermentation product. After the fermenting organism is inoculated into the fermentation medium it passes through a number of phases. The initial phase is referred to as the "lag phase" and is a period of adaptation where no significant amount of fermentation product is produced. During the next two phases referred to as the "exponential phase" with increased growth and the "stationary phase", which is the phase after maximum growth, significant amounts of fermentation product are produced. Fermentation cycles typically can go on for up to 96 hours or more, making each cycle time consuming and expensive.

The processes for producing fermentation products from lignocellulose-containing materials or cellulosic "biomass" is also limited by the tolerance of the fermenting organism to the many toxins found in the crude hydrolyzates used in the fermentation process. Removal of the toxins from the hydrolyzate is difficult, time consuming, and expensive. To avoid the costly toxin removal step, the percentage of solids in the hydrolyzates is conventionally kept below 10% total solids (w/w), thus minimizing the effect of the toxins on the fermenting organism. Unfortunately, limitation of total solids concentration means less available fermentation substrate and lower fermentation product yield per batch.

Thus, it is highly desirable to utilize crude hydrolyzates with high total solids concentration and decrease fermentation time necessary for producing a desired fermentation product from lignocellulose-containing material.

SUMMARY OF THE INVENTION

The invention relates to methods for producing fermentation products from lignocellulose-containing material using one or more fermenting organisms.

The invention relates to methods for producing fermentation products from lignocellulose-containing material, wherein the method comprises:
  i) pre-treating lignocellulose-containing material;
  ii) hydrolyzing pre-treated lignocellulose-containing material;
  iii) fermenting using a fermenting organism;

wherein fermentation is initiated and carried out at
  a) a fermentation organism cell count in the range from $10\text{-}250 \times 10^{10}$ cells per L fermentation medium; or
  b) a fermentation organism concentration in the range from 2-90 g dry weight fermenting organism per L fermentation medium.

DETAILED DESCRIPTION OF THE INVENTION

Figure 1:
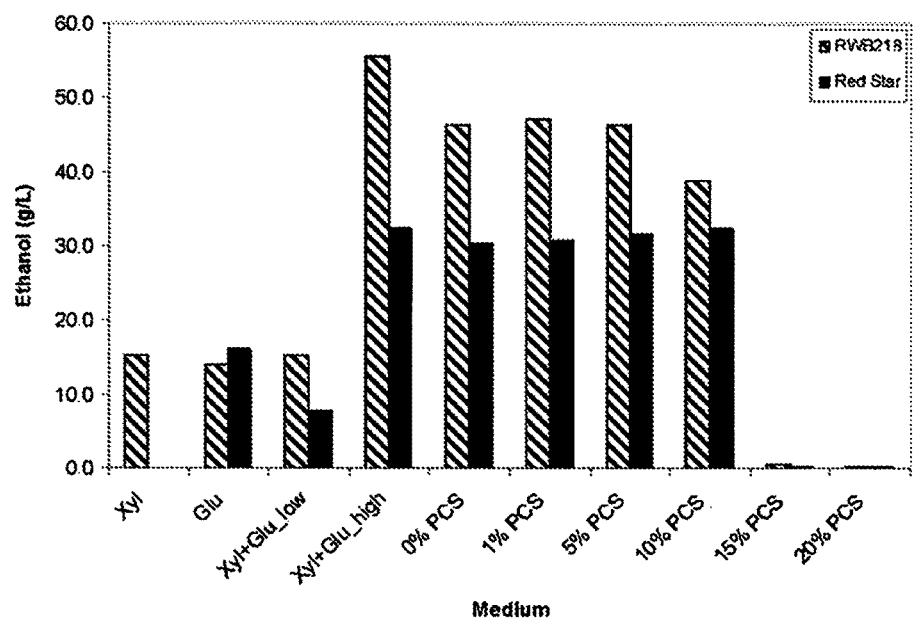
FIG. 1 demonstrates the effect of various amounts of sugar solutions and filtered, pre-treated corn stover (PCS) enzyme hydrolyzate on batch fermentation ethanol production in two different yeast strains after 96 hours.

The invention relates to methods for producing fermentation products from lignocellulose-containing material using one or more fermenting organisms.

According to the present invention, the fermentation time can be significantly shortened by carrying out fermentation at a very high cell count throughout fermentation. Even though the fermentation rate per fermenting organism may not be higher than in conventional fermentation processes the fact that the absolute number of fermenting organisms is high throughout fermentation results in a fast production (determined as absolute amount of fermentation product per time unit) of the desired fermentation product.

Further, according to the invention the fermenting organism may be recovered and re-used as described below. The shortened fermentation time and optional re-use of fermentation organisms reduces the overall cost of the methods of the present invention as compared to conventional methods.

Consequently, the invention relates to methods for producing fermentation products from lignocellulose-containing material, wherein the method comprises:

i) pre-treating lignocellulose-containing material;

ii) hydrolyzing pre-treated lignocellulose-containing material;

iii) fermenting using a fermenting organism;

wherein fermentation is initiated and carried out at:

a) a fermentation organism cell count in the range from $10\text{-}250 \times 10^{10}$ cells per L fermentation medium; or b) a fermentation organism concentration in the range from 2-90 g dry weight fermenting organism per L fermentation medium.

In a preferred embodiment in-soluble solids (including lignin and unconverted polysaccharides) are removed before fermentation. For instance, the in-soluble solids may be removed alter pre-treating the lignocellulose-containing material in step i). The pre-treated lignocellulose derived material, having in-soluble solids removed, may then be fermented in accordance with the invention. In another embodiment the in-soluble solids may be removed after hydrolyzing the pre-treated lignocellulose-containing material in step ii). The hydrolyzed pre-treated lignocellulose derived material, having in-soluble solids removed, may then be fermented in accordance with the invention.

The lignocellulose derived fermentable sugars to be fermented are in the form of liquor (e.g., filtrate) coming from the pre-treatment or hydrolysis steps i) or ii), or from both steps i) and, ii). In a preferred embodiment, hydrolysis in step ii) and fermentation in step iii) are carried out as separate hydrolysis and fermentation steps (SHE), as hybrid hydrolysis and fermentation step (HHF) or as a simultaneous hydrolysis and fermentation step (SSF). SSF, HHF and SHF steps are well known in the art.

In a preferred embodiment fermentation may be carried out at a fermentation organism cell count in the range from between $20\text{-}250 \times 10^{10}$ cells per L fermentation medium, more preferably in the range from $50\text{-}250 \times 10^{10}$ cells per L fermentation medium, more preferably in the range from $100\text{-}250 \times 10^{10}$ cells per L fermentation medium, more preferably in the range from $150\text{-}250 \times 10^{10}$ cells per L fermentation medium, such as in the range from $200\text{-}250 \times 10^{10}$ cells per L fermentation medium.

In a preferred embodiment fermentation may be carried out at a fermentation organism concentration in the range from 3-90 g dry weight fermenting organism per L fermentation medium, 3-50 g dry weight fermenting organism per L fermentation medium, preferably in the range from 4-50 g dry weight fermenting organism per L fermentation medium, preferably in the range from 5-50 g dry weight fermenting organism per L fermentation medium, more preferably in the range from 10-50 g dry weight fermenting organism per L fermentation medium, more preferably in the range from 10-40 g dry weight fermenting organism per L fermentation medium; especially in the range from 10-30 g dry weight fermenting organism per L fermentation medium.

According to the invention the fermenting organisms may be immobilized. For instance, the fermenting organisms may be immobilized on inert, high surface area supports which are suspended in the fermentation tank/vessel through which hydrolysed and/or pre-treated lignocellulose derived material to be fermented is fed. Any immobilization technique may be used according to the invention. Techniques for immobilizing fermenting organisms are well known in the art. Examples of suitable immobilizing techniques can be found in, e.g., Kesava et al., 1996, "Ethanol production by immobilized whole cells of *Zymomonas mobilis* in a continuous flow expanded bed bioreactor and a continuous flow stirred tank bioreactor", Journal of Industrial Microbiology 17:11-14; Gough et al., 1998, "Production of ethanol from molasses at 45 degrees C. using *Kluyveromyces marxianus* IMB3 immobilized in calcium alginate gels and poly(vinyl alcohol) cryogel", Bioprocess Engineering 19:87-90; Love et al., 1998, "Continuous ethanol fermentation at 45 degrees C. using *Kluyveromyces marxianus* IMB3 immobilized in Calcium alginate and kissiris", Bioprocess Engineering 18:187-189; Abbi at al., 1996, "Bioconversion of pentose sugars to ethanol by free and immobilized cells of *Candida shehatae* (NCL-3501): Fermentation behaviour" Process Biochemistry 31:555-560: Krishnan et al. 2000, "Ethanol production from glucose and xylose by immobilized *Zymomonas mobilis* CP4 (pZB5)", Applied Biochemistry And Biotechnology 84.6: 525-541; Chibata et al., 1981, Ann. Rev. Microphys. Bioeng 10: 197-216; Fukui et al., 1982. Ann. Rev. Microbial 36: 145-172; John F. Kennedy, 1982, Nature, 299: 777-778 (all refs are hereby incorporated by reference).

In one embodiment, the fermenting organisms may advantageously be recovered and re-used. For instance, the fermenting organisms may be recovered by separating them from the fermentation medium in the fermentation tank/vessel. Alternatively, the fermenting organisms may be recovered by separating them from the fermentation medium after fermentation. The fraction of the fermentation medium that contains the fermentation product may be further processed or recovered, e.g., by distillation. The recovered fermentation organisms may be recycled to the same fermentation tank/vessel or to one or more other fermentation tanks/vessels. In other words, the fermenting organisms may be recovery and recycled to the fermentation medium and this way re-used in one or more additional fermentation cycles in accordance with the invention. The number of fermentation cycles in which the recycled fermenting organisms can be used may be dependent upon a number of factors including, but not limited to, pH, type of fermenting organism, fermentation product concentration such as ethanol concentration, or concentration of total solids (TS). Those skilled in the art can alter these factors in accordance with the invention to optimize the number of recycling events.

In another embodiment, a propagation step may be added to the process of recovering and recycling the fermenting organisms. For example, the recovered fermenting organism may be propagated for a period of time prior to recycling or re-using it in a subsequent fermentation cycle.

Any technique may be used for recovering the fermenting organisms. Suitable techniques well known in the art include filtration. e.g., using a filter press, and centrifugation.

According to a preferred embodiment an enzyme capable of converting xylose to xylulose may be present during hydrolysis and/or fermentation. Such xylose-to-xylulose converting enzyme may in a preferred embodiment be a xylose isomerase (sometimes referred to as glucose isomerase). Examples of suitable xylose isomerases can be found in the "Xylose Isomerase" section below. Converting xylose to xylulose is advantageous as it allows some commonly used C6 fermenting organisms, such as *Saccharomyces cerevisiae*, to convert xylulose to the desired fermentation product, such as ethanol, simultaneously with fermenting C6 sugars, such as especially glucose.

In one embodiment, the fermentation of C6 and C5 fermentable sugars is carried out simultaneously. The simultaneous fermentation of C5 and C6 sugars may be carried out as follows:

The fermentation step iii) further comprises:

a) simultaneous fermentation of C5 and C6 sugars derived from pre-treatment step i) or hydrolysis step ii);

b) fermenting organisms are recovered and recycled.

Alternatively, in another embodiment, the hydrolysis step ii) and fermentation step iii) further comprise:

1) simultaneous hydrolysis and simultaneous fermentation of C5 and C6 sugars derived from pre-treatment step i).

In another embodiment, the hydrolysis step ii) and fermentation step iii) further comprise:

1) simultaneous hydrolysis and simultaneous fermentation of C5 and C6 sugars derived from pre-treatment step i);
2) fermenting organisms are recovered and recycled.

Alternatively, in another embodiment, fermentation of C5 fermentable sugars is carried out subsequent to fermentation of C6 fermentable sugars. Subsequent fermentation of C6 and C5 sugars may be carried out as follows:

The fermentation step iii) further comprises:
a) fermentation of C6 sugars derived from pre-treatment step i) or hydrolysis step ii);
b) C6 fermenting organisms are recovered and recycled;
c) C5 sugars are fermented;
d) C5 fermenting organisms are recovered and recycled.

Alternatively, in another embodiment, the hydrolysis step ii) and fermentation step iii) further comprises:
1) simultaneous hydrolysis and fermentation of C6 sugars derived from pre-treatment step i);
2) C5 sugars are fermented.

Alternatively, in another embodiment, the hydrolysis step ii) and fermentation step iii) further comprises:
1) simultaneous hydrolysis and fermentation of C6 sugars derived from pre-treatment step i);
2) in-soluble solids are removed;
3) C5 sugars are fermented;
4) fermenting organisms are recovered and recycled.

In an embodiment the lignocellulose-containing material may be detoxified. In an embodiment the material is washed before hydrolysis and/or fermentation. In another embodiment the lignocellulose-containing material may be un-detoxified, such as un-washed.

Lignocellulose-Containing Material

"Lignocellulose" or "lignocellulose-containing material" means material primarily consisting of cellulose, hemicellulose, and lignin. Such material is often referred to as "biomass."

Lignocellulosic biomass is a complex structure of cellulose fibers wrapped in a lignin and hemicellulose sheath. The structure of lignocellulose is such that it is not susceptible to enzymatic hydrolysis. In order to enhance enzymatic hydrolysis, the lignocellulose has to be pre-treated, e.g., by acid hydrolysis under adequate conditions of pressure and temperature, in order to break the lignin seal, saccharify and solubilize the hemicellulose, and disrupt the crystalline structure of the cellulose. The cellulose can then be hydrolyzed enzymatically, e.g., by cellutolytic enzyme treatment, to convert the carbohydrate polymers into fermentable sugars which may be fermented into a desired fermentation product, such as ethanol. Hemicellulolytic enzyme treatments may also be employed to hydrolyze any remaining hemicellulose in the pre-treated biomass.

The lignocellulose-containing material may be any material containing lignocellulose. In a preferred embodiment the lignocellulose-containing material contains at least 30 wt. %, preferably at least 50 wt. %, more preferably at least 70 wt. %, even more preferably at least 90 wt. %, lignocellulose. It is to be understood that the lignocellulose-containing material may also comprise other constituents such as proteinaceous material, starch, and sugars such as fermentable or un-fermentable sugars or mixtures thereof.

Lignocellulose-containing material is generally found, for example, in the stems, leaves, hulls, husks, and cobs of plants or leaves, branches, and wood of trees. Lignocellulose-containing material includes, but is not limited to, herbaceous material, agricultural residues, forestry residues, municipal solid wastes, waste paper, and pulp and paper mill residues. It is to be understood that lignocellulose-containing material may be in the form of plant cell wall material containing lignin, cellulose, and hemicellulose in a mixed matrix.

In a preferred embodiment the lignocellulose-containing material is selected from one or more of corn fiber, rice straw, pine wood, wood chips, poplar, bagasse, and paper and pulp processing waste.

Other examples of suitable lignocellulose-containing material include corn stover, corn cobs, hard wood such as poplar and birch, soft wood, cereal straw such as wheat straw, switch grass, Miscanthus, rice hulls, municipal solid waste (MSW), industrial organic waste, office paper, or mixtures thereof.

In a preferred embodiment the lignocellulose-containing material is corn stover or corn cobs. In another preferred embodiment, the lignocellulose-containing material is corn fiber. In another preferred embodiment, the lignocellulose-containing material is switch grass. In another preferred embodiment, the lignocellulose-containing material is bagasse.

Pre-Treatment

The lignocellulose-containing material may be pre-treated in any suitable way.

Pre-treatment is carried out before hydrolysis or fermentation. The goal of pre-treatment is to separate or release cellulose, hemicellulose, and lignin and this way improves the rate or efficiency of hydrolysis. Pre-treatment methods including wet-oxidation and alkaline pre-treatment target lignin release, while dilute acid treatment and auto-hydrolysis target hemicellulose release. Steam explosion is an example of pre-treatment that targets cellulose release.

According to the invention the pre-treatment step may be a conventional pre-treatment step using techniques well known in the art. In a preferred embodiment pre-treatment takes place in aqueous slurry. The lignocellulose-containing material may during pre-treatment be present in an amount between 10-80 wt. %, preferably between 20-70 wt. %, especially between 30-60 wt. %, such as around 50 wt. %.

Chemical, Mechanical and/or Biological Pre-Treatment

According to the invention, the lignocellulose-containing material may be pre-treated chemically, mechanically, biologically, or any combination thereof, before or during hydrolysis.

Preferably the chemical, mechanical or biological pre-treatment is carried out prior to the hydrolysis. Alternatively, the chemical, mechanical or biological pre-treatment may be carried out simultaneously with hydrolysis, such as simultaneously with addition of one or more cellulolytic enzymes, or other enzyme activities, to release, e.g., fermentable sugars, such as glucose or maltose.

In an embodiment of the invention the pre-treated lignocellulose-containing material may be washed or detoxified in another way. However, washing or detoxification is not required. In a preferred embodiment, the pre-treated lignocellulose-containing material is not washed or detoxified.

Chemical Pre-Treatment

The phrase "chemical pre-treatment" refers to any chemical pre-treatment which promotes the separation or release of cellulose, hemicellulose, or lignin. Examples of suitable chemical pre-treatment methods include treatment with, for example, dilute acid, lime, alkaline, organic solvent, ammonia, sulfur dioxide, or carbon dioxide. Further, wet oxidation and pH-controlled hydrothermolysis are also considered chemical pre-treatment.

In a preferred embodiment the chemical pre-treatment is acid treatment, more preferably, a continuous dilute or mild acid treatment such as treatment with sulfuric acid, or another organic acid such as acetic acid, citric acid, tartaric acid, succinic acid, hydrogen chloride or mixtures thereof. Other acids may also be used. Mild acid treatment means that the treatment pH lies in the range from pH 1-5, preferably pH 1-3. In a specific embodiment the acid concentration is in the range from 0.1 to 2.0 wt. % acid and is preferably sulphuric acid. The acid may be contacted with the lignocellulose-containing material and the mixture may be held at a temperature in the range of 160-220° C., such as 165-195° C., for periods ranging from minutes to seconds, e.g., 1-60 minutes, such as 2-30 minutes or 3-12 minutes. Addition of strong acids such as sulphuric acid may be applied to remove hemicellulose. Such addition of strong acids enhances the digestibility of cellulose.

Other chemical pre-treatment techniques are also contemplated according to the invention. Cellulose solvent treatment has been shown to convert about 90% of cellulose to glucose. It has also been shown that enzymatic hydrolysis could be greatly enhanced when the lignocellulose structure is disrupted. Alkaline $H_2O_2$, ozone, organosolv (using Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier at al., 2005, Bioresource Technology 96: 673-686).

Alkaline chemical pre-treatment with base, e.g., NaOH, $Na_2CO_3$ and ammonia or the like, is also contemplated according to the invention. Pre-treatment methods using ammonia are described in, e.g., WO 2006/110891, WO 2006/11899, WO 2006/11900, WO 2006/110901, which are hereby incorporated by reference.

Wet oxidation techniques involve the use of oxidizing agents such as sulphite based oxidizing agents or the like. Examples of solvent pre-treatments include treatment with DMSO (dimethyl sulfoxide) or the like. Chemical pre-treatment is generally carried out for 1 to 60 minutes, such as from 5 to 30 minutes, but may be carried out for shorter or longer periods of time depending on the material to be pre-treated.

Other examples of suitable pre-treatment methods are described by Schell at al., 2003, Appl. Biochem and Biotechn. Vol. 105-108, p. 69-85, and Mosier et al., 2005, Bioresource Technology 96: 673-686, and U.S. Application Publication No. 2002/0164730, each of which are hereby incorporated by reference.

Mechanical Pre-Treatment

The phrase "mechanical pre-treatment" refers to any mechanical or physical pre-treatment which promotes the separation or release of cellulose, hemicellulose, or lignin from lignocellulose-containing material. For example, mechanical pre-treatment includes various types of milling, irradiation, steaming/steam explosion, and hydrothermolysis.

Mechanical pre-treatment includes comminution, i.e., mechanical reduction of the size. Comminution includes dry milling, wet milling and vibratory ball milling. Mechanical pre-treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C. preferably from about 140 to 235° C. In a preferred embodiment mechanical pre-treatment is a batch-process, steam gun hydrolyzer system which uses high pressure and high temperature as defined above. A Sunds Hydrolyzer (available from Sunds Defibrator AB (Sweden) may be used for this.

Combined Chemical and Mechanical Pre-Treatment

In a preferred embodiment the lignocellulose-containing material is pre-treated both chemically and mechanically. For instance, the pre-treatment step may involve dilute or mild acid treatment and high temperature and/or pressure treatment. The chemical and mechanical pre-treatments may be carried out sequentially or simultaneously, as desired.

Accordingly, in a preferred embodiment, the lignocellulose-containing material is subjected to both chemical and mechanical pre-treatment to promote the separation or release of cellulose, hemicellulose or lignin.

In a preferred embodiment pre-treatment is carried out as a dilute or mild acid steam explosion step. In another preferred embodiment pre-treatment is carried out as an ammonia fiber explosion step (or AFEX pre-treatment step).

Biological Pre-Treatment

The phrase "biological pre-treatment" refers to any biological pre-treatment which promotes the separation or release of cellulose, hemicellulose, or lignin from the lignocellulose-containing material. Biological pre-treatment techniques can involve applying lignin-solubilizing microorganisms. See, for example, Hsu, T.-A., 1996. Pretreatment of biomass, in *Handbook on Bioethanol: Production and Utilization*, Wyman, C. E., ed., Taylor & Francis, Washington, D.C., 179-212; Ghosh, P., and Singh, A, 1993, Physicochemical and biological treatments for enzymatic/microbial conversion of lignocellulosic biomass, *Adv. Appl. Microbial.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Theo, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolyzates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95.

Hydrolysis

Before the pre-treated lignocellulose-containing material is fermented it may be hydrolyzed to break down cellulose and hemicellulose into fermentable sugars. In a preferred embodiment the pre-treated material is hydrolyzed, preferably enzymatically, before fermentation.

The dry solids content during hydrolysis may be in the range from 5-50 wt. %, preferably 10-40 wt. %, preferably 20-30 wt. %. Hydrolysis may in a preferred embodiment be carried out as a fed batch process where the pre-treated lignocellulose-containing material (i.e., the substrate) is fed gradually to, e.g., an enzyme containing hydrolysis solution.

In a preferred embodiment hydrolysis is carried out enzymatically. According to the invention the pre-treated lignocellulose-containing material may be hydrolyzed by one or more cellulolytic enzymes, such as cellulases or hemicellulases, or combinations thereof.

In a preferred embodiment hydrolysis is carried out using a cellulolytic enzyme preparation comprising one or more polypeptides having cellulolytic enhancing activity. In a preferred embodiment the polypeptide(s) having cellulolytic enhancing activity is(are) of family GH61A origin. Examples of suitable and preferred cellulolytic enzyme preparations and polypeptides having cellulolytic enhancing activity are described in the "Cellulolytic Enzymes" section and "Cellulotytic Enhancing Polypeptides" section below.

As the lignocellulose-containing material may contain constituents other than lignin, cellulose and hemicellulose, hydrolysis and/or fermentation in steps ii) and iii) may be carried out in the presence of additional enzyme activities such as protease activity, amylase activity, carbohydrate-generating enzyme activity, and esterase activity such as lipase activity.

Enzymatic hydrolysis is preferably carried out in a suitable aqueous environment under conditions which can readily be determined by one skilled in the art. In a preferred embodiment hydrolysis is carried out at suitable, preferably optimal, conditions for the enzyme(s) in question.

Suitable process time, temperature and pH conditions can readily be determined by one skilled in the art. Preferably, hydrolysis is carried out at a temperature between 25 and 70° C., preferably between 40 and 60° C., especially around 50° C. The step is preferably carried out at a pH in the range from pH 3-8, preferably pH 4-6, especially around pH 5. Hydrolysis is typically carried out for between 12 and 96 hours, preferable 16 to 72 hours, more preferably between 24 and 48 hours.

Fermentation

According to the invention fermentable sugars from pretreated and/or hydrolyzed lignocellulose-containing material may be fermented by one or more fermenting organisms capable of fermenting sugars, such as glucose, xylose, mannose, and galactose directly or indirectly into a desired fermentation product. The fermentation conditions depend on the desired fermentation product and fermenting organism and can easily be determined by one of ordinary skill in the art.

Especially in the case of ethanol fermentation the fermentation may be ongoing for between 1-48 hours, preferably 1-24 hours. In an embodiment the fermentation is carried out at a temperature between 20 to 40° C., preferably 26 to 34° C., in particular around 32° C. In one embodiment, the pH is greater than 5. In another embodiment, the pH is from pH 3-7, preferably 4-6. However, some, e.g., bacterial fermenting organisms have higher fermentation temperature optima. Therefore, in an embodiment the fermentation is carried out at temperature between 40-60° C., such as 50-60° C. The skilled person in the art can easily determine suitable fermentation conditions.

Fermentation can be carried out in a batch, fed-batch, or continuous reactor. Fed-batch fermentation may be fixed volume or variable volume fed-batch. In one embodiment, fed-batch fermentation is employed. The volume and rate of fed-batch fermentation depends on, for example, the fermenting organism, the identity and concentration of fermentable sugars, and the desired fermentation product. Such fermentation rates and volumes can readily be determined by one of ordinary skill in the art.

SSF, HHF and SHE

In one embodiment of the present invention, hydrolysis and fermentation is carried out as a simultaneous hydrolysis and fermentation step (SSF). In general this means that combined/simultaneous hydrolysis and fermentation are carried out at conditions (e.g., temperature and/or pH) suitable, preferably optimal, for the fermenting organism(s) in question.

In another embodiment hydrolysis step and fermentation step are carried out as hybrid hydrolysis and fermentation (HHF). HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step).

In another embodiment, the hydrolysis and fermentation steps may also be carried out as separate hydrolysis and fermentation, where the hydrolysis is taken to completion before initiation of fermentation. This is often referred to as "SHF".

Recovery

Subsequent to fermentation the fermentation product may optionally be separated from the fermentation medium in any suitable way. For instance, the medium may be distilled to extract the fermentation product or the fermentation product may be extracted from the fermentation medium by micro or membrane filtration techniques. Alternatively the fermentation product may be recovered by stripping. Recovery methods are well known in the art, Fermentation Products The present invention may be used for producing any fermentation product. Preferred fermentation products include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

Other products include consumable alcohol industry products, e.g., beer and wine; dairy industry products, e.g., fermented dairy products; leather industry products and tobacco industry products. In a preferred embodiment the fermentation product is an alcohol, especially ethanol. The fermentation product, such as ethanol, obtained according to the invention, may preferably be used as fuel alcohol/ethanol. However, in the case of ethanol it may also be used as potable ethanol.

Fermenting Organism

The phrase "fermenting organism" refers to any organism, including bacterial and fungal organisms, suitable for producing a desired fermentation product. The fermenting organism may be C6 or C5 fermenting organisms, or a combination thereof. Both C6 and C5 fermenting organisms are well known in the art.

Suitable fermenting organisms are able to ferment, i.e., convert, fermentable sugars, such as glucose, fructose, maltose, xylose, mannose and or arabinose, directly or indirectly into the desired fermentation product.

Examples of fermenting organisms include fungal organisms such as yeast. Preferred yeast includes strains of the genus *Saccharomyces*, in particular strains of *Saccharomyces cerevisiae* or *Saccharomyces uvarum*; a strain of *Pichia*, preferably *Pichia stipitis* such as *Pichia stipitis* CBS 5773 or *Pichia pastoris*; a strain of the genus *Candida*, in particular a strain of *Candida utilis, Candida arabinofermentans, Candida diddensil, Candida sonorensis, Candida shehatae, Candida tropicalis*, or *Candida boidinii*. Other fermenting organisms include strains of *Hansenula*, in particular *Hansenula polymorpha* or *Hansenula anomala; Kluyveromyces*, in particular *Kluyveromyces fragilis* or *Kluyveromyces marxianus*; and *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobacter palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes* and strains of *Thermoanaerobacter*, in particular *Thermoanaerobacter* BG1L1 (*Appl. Microbial. Biotech.* 77: 61-86) and *Thermoanarobacter ethanolicus*, *Thermoanaerobacter thermosaccharolyticum*, or *Thermoanaerobacter mathranii*, Strains of *Lactobacillus* are also envisioned as are strains of *Corynebacterium glutamicum R*, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In connection with fermentation of lignocellulose derived materials, C5 sugar fermenting organisms are contemplated. Most C5 sugar fermenting organisms also ferment C6 sugars. Examples of C5 sugar fermenting organisms include strains of *Pichia*, such as of the species *Pichia stipitis*. C5 sugar fermenting bacteria are also known. Also some *Saccharomyces cerevisiae* strains ferment C5 (and C6) sugars. Examples are genetically modified strains of *Saccharomyces* spp. that are capable of fermenting C5 sugars include the ones concerned in, e.g., Ho et al., 1998, Applied and Environmental Microbiology, p. 1852-1859 and Karhumaa et al, 2006, *Microbial Cell Factories* 5:18, and Kuyper et al., 2005, *FEMS Yeast Research* 5, p. 925-934.

Certain fermenting organisms' fermentative performance may be inhibited by the presence of inhibitors in the fermentation media and thus reduce ethanol production capacity. Compounds in biomass hydrosylates and high concentrations of ethanol are known to inhibit the fermentative capacity of certain yeast cells. Pre-adaptation or adaptation methods may reduce this inhibitory effect. Typically pre-adaptation or adaptation of yeast cells involves sequentially growing yeast cells, prior to fermentation, to increase the fermentative performance of the yeast and increase ethanol production. Methods of yeast pre-adaptation and adaptation are known in the art. Such methods may include, for example, growing the yeast cells in the presence of crude biomass hydrolyzates; growing yeast cells in the presence of inhibitors such as phenolic compounds, furaldehydes and organic acids; growing yeast cells in the presence of non-inhibiting amounts of ethanol; and supplementing the yeast cultures with acetaldehyde. In one embodiment, the fermenting organism is a yeast strain subject to one or more pre-adaptation or adaptation methods prior to fermentation.

Certain fermenting organisms such as yeast require an adequate source of nitrogen for propagation and fermentation. Many sources of nitrogen can be used and such sources of nitrogen are well known in the art. In one embodiment, a low cost source of nitrogen is used. Such low cost sources can be organic, such as urea, DDGs, wet cake or corn mash, or inorganic, such as ammonia or ammonium hydroxide.

Commercially available yeast suitable for ethanol production includes, e.g., ETHANOL RED™ yeast (available from Fermentis/Lesaffre, USA), FALI™ (available from Fleischmann's Yeast, USA) SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Fermentation Medium

The phrase "fermentation media" or "fermentation medium" refers to the environment in which fermentation is carried out and comprises the fermentation substrate, that is, the carbohydrate source that is metabolized by the fermenting organism(s), and may include the fermenting organism(s).

The fermentation medium may comprise nutrients and growth stimulator(s) for the fermenting organism(s). Nutrient and growth stimulators are widely used in the art of fermentation and include nitrogen sources, such as ammonia; vitamins and minerals, or combinations thereof.

Following fermentation, the fermentation media or fermentation medium may further comprise the fermentation product.

Enzymes

Even if not specifically mentioned in context of a method or process of the invention, it is to be understood that the enzyme(s) as well as other compounds are used in an effective amount.

Cellulolytic Activity

The phrase "cellulolytic activity" as used herein are understood as comprising enzymes having cellobiohydrolase activity (EC 3.2.1.91), e.g., cellobiohydrolase I and cellobiohydrolase II, as well as endoglucanase activity (EC 3.2.1.4) and beta-glucosidase activity (EC 3.2.1.21).

At least three categories of enzymes are important for converting cellulose into fermentable sugars: endo-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases seems to be the key enzymes for degrading native crystalline cellulose.

The cellulolytic activity may, in a preferred embodiment, be in the form of a preparation of enzymes of fungal origin, such as from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium kicknowense*.

In preferred embodiment the cellulolytic enzyme preparation contains one or more of the following activities: cellulase, hemicellulase, cellulolytic enzyme enhancing activity, beta-glucosidase activity, endoglucanase, cellubiohydrolase, or xylose isomerase.

In a preferred embodiment the cellulase may be a composition as defined in PCT/US2008/065417, which is hereby incorporated by reference. Specifically, in one embodiment is the cellulase composition used in Example 1 (Cellulase preparation A) described below. In a preferred embodiment the cellulolytic enzyme preparation comprising a polypeptide having cellulolytic enhancing activity, preferably a family GH61A polypeptide, preferably the one disclosed in WO 2005/074656 (Novozymes). The cellulolytic enzyme preparation may further comprise a beta-glucosidase, such as a beta-glucosidase derived from a strain of the genus *Trichoderma*, *Aspergillus* or *Penicillium*, including the fusion protein having beta-glucosidase activity disclosed in WO 2008/057637. In a preferred embodiment the cellulolytic enzyme preparation may also comprises a CBH II enzyme, preferably *Thielavia terrestris* cellobiohydrolase II CEL6A. In another preferred embodiment the cellulolytic enzyme preparation may also comprise cellulolytic enzymes, preferably one derived from *Trichoderma teasel* or *Humicola insolens*.

The cellulolytic enzyme preparation may also comprising a polypeptide having cellulolytic enhancing activity (GH61A) disclosed in WO 2005/074656; a beta-glucosidase (fusion protein disclosed in WO 2008/057637) and cellulolytic enzymes derived from *Trichoderma reesei*.

In an embodiment the cellulolytic enzyme is the commercially available product CELLUCLAST® 1.5L or CELLUZYME™ available from Novozymes A/S, Denmark or ACCELERASE™ 1000 (from Genencor Inc., USA).

A cellulolytic enzyme may be added for hydrolyzing the pre-treated lignocellulose-containing material. The cellulolytic enzyme may be dosed in the range from 0.1-100 FPU per gram total solids (TS), preferably 0.5-50 FPU per gram TS, especially 1-20 FPU per gram TS. In another embodiment at least 0.1 mg cellulolytic enzyme per gram total solids (TS), preferably at least 3 mg cellulolytic enzyme per gram TS, such as between 5 and 10 mg cellulolytic enzyme(s) per gram TS is(are) used for hydrolysis.

Endoglucanase (EG)

The term "endoglucanase" means an endo-1,4-(1,3;1,4)-beta-D-glucan 4-glucanohydrolase (E.C. No. 3.2.1.4), which catalyses endo-hydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity may be determined using carboxymethyl cellulose (CMC) hydrolysis according to the procedure of Ghose, 1987, *Pure and Appl. Chem.* 59: 257-268.

In a preferred embodiment endoglucanases may be derived from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

Cellobiohydrolase (CBH)

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydroloses are mentioned above including CBH I and CBH II from *Trichoderma reseei*; *Humicola insolens* and CBH II from *Thielavia terrestris* cellobiohydrolase (CELL6A).

Cellobiohydrolase activity may be determined according to the procedures described by Lever at al., 1972, *Anal. Biochem.* 47: 273-279 and by van Tilbeurgh at, 1982, *FEBS Letters* 149: 152-156; van Tilbeurgh and Claeyssens, 1985, *FEBS Letters* 187: 283-288. The Lever et al. method is suitable for assessing hydrolysis of cellulose in corn stover and the method of van Tilbeurgh et al. is suitable for determining the cellobiohydrolase activity on a fluorescent disaccharide derivative.

Beta-Glucosidase

One or more beta-glucosidases may be present during hydrolysis.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi at al., 2002, *J. Basic Microblol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

In a preferred embodiment the beta-glucosidase is of fungal origin, such as a strain of the genus *Trichoderma*, *Aspergillus* or *Penicillium*. In a preferred embodiment the beta-glucosidase is a derived from *Trichoderma reesei*, such as the beta-glucosidase encoded by the bgl1 gene (see FIG. 1 of EP 562003). In another preferred embodiment the beta-glucosidase is derived from *Aspergillus oryzae* (recombinantly produced in *Aspergillus oryzae* according to WO 2002/095014), *Aspergillus fumigatus* (recombinantly produced in *Aspergillus oryzae* according to Example 22 of WO 2002/095014) or *Aspergillus niger* (1981, J. Appl. Vol 3, pp 157-163).

Hemicellulase

Hemicellulose can be broken down by hemicellulases and/or acid hydrolysis to release its five and six carbon sugar components.

In an embodiment of the invention the lignocellulose derived material may be treated with one or more hemicellulase.

Any hemicellulase suitable for use in hydrolyzing hemicellulose, preferably into xylose, may be used. Preferred hemicellulases include xylanases, arabinofuranosidases, acetyl xylan esterase, feruloyl esterase, glucuronidases, endo-gatactanase, mannases, endo or exo arabinases, exo-galactanses, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

In an embodiment the hemicellulase is a xylanase. In an embodiment the xylanase may preferably be of microbial origin, such as of fungal origin (e.g., *Trichoderma, Meripilus, Humicola, Aspergillus, Fusarium*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH10 or GH11. Examples of commercial xylanases include SHEARZYME™ and BIOFEED WHEAT™ from Novozymes A/S, Denmark.

The hemicellulase may be added in an amount effective to hydrolyze hemicellulose, such as, in amounts from about 0.001 to 0.5 wt. % of total solids (TS), more preferably from about 0.05 to 0.5 wt. % of TS.

Xylanases may be added in amounts of 0.001-1.0 g/kg DM (dry matter) substrate, preferably in the amounts of 0.005-0.5 g/kg DM substrate, and most preferably from 0.05-0.10 g/kg DM substrate.

Xylose Isomerase

Xylose isomerases (D-xylose ketoisomerase) (E.C. 5.3.1.5.) are enzymes that catalyze the reversible isomerization reaction of D-xylose to D-xylulose. Some xylose isomerases also convert the reversible isomerization of O-glucose to D-fructose. Therefore, xylose isomarase is sometimes referred to as "glucose isomerase."

A xylose isomerase used in a method or process of the invention may be any enzyme having xylose isomerase activity and may be derived from any sources, preferably bacterial or fungal origin, such as filamentous fungi or yeast. Examples of bacterial xylose isomerases include the ones belonging to the genera *Streptomyces, Actinoplanes, Bacillus* and *Flavobacterium*, and *Thermotoga*, including *T. neapolitana* (Vieille et al., 1995, Appl. Environ. Microbiol. 61 (5), 1867-1875) and *T. maritime*.

Examples of fungal xylose isomerases are derived species of *Basidiomycetes*.

A preferred xylose isomerase is derived from a strain of yeast genus *Candida*, preferably a strain of *Candida boidinii*, especially the *Candida boidinii* xylose isomerase disclosed by, e.g., Vongsuvanlert et al., 1988, Agric. Biol. Chem., 52(7): 1817-1824. The xylose isomerase may preferably be derived from a strain of *Candida boidinii* (*Kloeckera* 2201), deposited as DSM 70034 and ATCC 48180, disclosed in Ogata at al., Agric. Biol. Chem, Vol. 33, p. 1519-1520 or Vongsuvanlert at al., 1988, Agric. Biol. Chem, 52(2), p. 1519-1520.

In one embodiment the xylose isomerase is derived from a strain of *Streptomyces*, e.g., derived from a strain of *Streptomyces murinus* (U.S. Pat. No. 4,687,742); *S. flavovirens, S. albus, S. achromogenus, S. echinatus, S. wedmorensis* all disclosed in U.S. Pat. No. 3,616,221. Other xylose isomerases are disclosed in U.S. Pat. No. 3,622,463, U.S. Pat. No. 4,351,903, U.S. Pat. No. 4,137,126, U.S. Pat. No. 3,625,828, HU patent no. 12,415, DE patent 2,417,642, JP patent no. 69,28,473, and WO 2004/044129 each incorporated by reference herein.

The xylose isomerase may be either in immobilized or liquid form. Liquid form is preferred.

Examples of commercially available xylose isomerases include SWEETZYME™ T from Novozymes A/S, Denmark.

The xylose isomerase is added to provide an activity level in the range from 0.01-100 IGIU per gram total solids.

Cellulolytic Enhancing Activity

The phrase "cellulolytic enhancing activity" is defined herein as a biological activity that enhances the hydrolysis of a lignocellulose derived material by proteins having cellulolytic activity. For purposes of the present invention, cellulolytic enhancing activity is determined by measuring the increase in reducing sugars or in the increase of the total of cellobiose and glucose from the hydrolysis of a lignocellulose derived material, e.g., pre-treated lignocellulose-containing material by cellulolytic protein under the following conditions: 1-50 mg of total protein/g of cellulose in PCS (pretreated corn stover), wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS).

The polypeptides having cellulolytic enhancing activity enhance the hydrolysis of a lignocellulose derived material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

In a preferred embodiment the hydrolysis and/or fermentation is carried out in the presence of a cellulolytic enzyme in combination with a polypeptide having enhancing activity. In a preferred embodiment the polypeptide having enhancing activity is a family GH61A polypeptide. WO 2005/074647 discloses isolated polypeptides having cellulolytic enhancing activity and polynucleotides thereof from *Thielavia terrestris*. WO 2005/074656 discloses an isolated polypeptide having cellulolytic enhancing activity and a polynucleotide thereof from *Thermoascus aurantiacus*. U.S. Application Publication No. 2007/0077630 discloses an isolated polypeptide having cellulolytic enhancing activity and a polynucleotide thereof from *Trichoderma reesei*.

Alpha-Amylase

According to the invention any alpha-amylase may be used. Preferred alpha-amylases are of microbial, such as bacterial or fungal origin. Which alpha-amylase is the most suitable depends on the process conditions but can easily be determined by one skilled in the art.

In one embodiment the preferred alpha-amylase is an acid alpha-amylase, e.g., fungal acid alpha-amylase or bacterial acid alpha-amylase. The phrase "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Aloha-Amylase

In another preferred embodiment the alpha-amylase is of *Bacillus* origin. The *Bacillus* alpha-amylase may preferably be derived from a strain of *B. licheniformis, B. amyloliquefaciens, B. subtilis* or *B. steamthermophilus*, but may also be derived from other *Bacillus* sp. Specific examples of contemplated alpha-amylases include the *Bacillus licheniformis* alpha-amylase shown in SEQ ID NO: 4 in WO 1999/19467, the *Bacillus amyloliquefaciens* alpha-amylase SEQ ID NO: 5 in WO 1999/19467 and the *Bacillus stearothermophilus* alpha-amylase shown in SEQ ID NO: 3 in WO 1999/19467 (all sequences hereby incorporated by reference). In an embodiment of the invention the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NO: 1, 2 or 3, respectively, in WO 1999/19467.

The *Bacillus* alpha-amylase may also be a variant and/or hybrid, especially one described in any of WO 1996/23873, WO 1996/23874, WO 1997/41213, WO 1999/19467, WO 2000/60059, and WO 2002/10355 (all documents hereby incorporated by reference). Specifically contemplated alpha-amylase variants are disclosed in U.S. Pat. No. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO: 3 disclosed in WO 1999/19467 or deletion of amino acids R179 and G180 using SEQ ID NO: 3 in WO 1999/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO:3 disclosed in WO 1999/19467.

Bacterial Hybrid Alpha-Amylase

A hybrid alpha-amylase specifically contemplated comprises 445 C-terminal amino acid residues of the *Bacillus licheniformis* alpha-amylase (shown in SEQ ID NO: 4 of WO 1999/19467) and the 37 N-terminal amino acid residues of the alpha-amylase derived from *Bacillus amyloliquefaciens* (shown in SEQ ID NO: 5 of WO 1999/19467), with one or more, especially all, of the following substitution: G48A+T49I+G107A+H156Y+A181T+N190F+I201F+A209V+Q264S (using the *Bacillus licheniformis* numbering in SEQ ID NO: 4 of WO 1999/19467). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 1999/19467).

Fungal Alpha-Amylase

Fungal alpha-amylases include alpha-amylases derived from a strain of the genus *Aspergillus*, such as, *Aspergillus oryzae*, *Aspergillus niger* and *Aspergillus kawachii* alpha-amylases.

A preferred acidic fungal alpha-amylase is a Fungamyl-like alpha-amylase which is derived from a strain of *Aspergillus oryzae*. According to the present invention, the phrase "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 1996/23874.

Another preferred acidic alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in WO 1989/01969 (Example 3). A commercially available acid fungal alpha-amylase derived from *Aspergillus niger* is SP288 (available from Novozymes A/S, Denmark).

Other contemplated wild-type alpha-amylases include those derived from a strain of the genera *Rhizomucor* and *Meripilus*, preferably a strain of *Rhizomucor pusillus* (WO 2004/055178 incorporated by reference) or *Meripilus giganteus*.

In a preferred embodiment the alpha-amylase is derived from *Aspergillus kawachii* and disclosed by Kaneko et al., 1996, J. Ferment. Bioeng. 81:292-298, "Molecular-cloning and determination of the nucleotide-sequence of a gene encoding an acid-stable alpha-amylase from *Aspergillus kawachii*"; and further as EMBL. #AB008370.

The fungal alpha-amylase may also be a wild-type enzyme comprising a starch-binding domain (SBD) and an alpha-amylase catalytic domain (i.e., none-hybrid), or a variant thereof. In an embodiment the wild-type alpha-amylase is derived from a strain of *Aspergillus kawachii*.

Fungal Hybrid Alpha-Amylase

In a preferred embodiment the fungal acid alpha-amylase is a hybrid alpha-amylase. Preferred examples of fungal hybrid alpha-amylases include the ones disclosed in WO 2005/003311 or U.S. Application Publication No. 2005/0054071 (Novozymes) or US patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO:100 in U.S. 60/638,614), *Rhizomucor pusillus* alpha-amylase with *Athelia rolfsii* AMG linker and SBD (SEQ ID NO: 101 in U.S. application No. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in U.S. application no. 60/638,614). Other specifically contemplated hybrid alpha-amylases are any of the ones listed in Tables 3, 4, 5, and 6 in Example 4 in U.S. application Ser. No. 11/316, 535 and WO 2006/069290, each hereby incorporated by reference.

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., more than 70%, more than 75%, more than 80%, more than 85%, more than 90%, more than 95%, more than 96%, more than 97%, more than 98%, more than 99% or even 100% identity to the mature enzyme sequences.

An acid alpha-amylases may according to the invention be added in an amount of 0.1 to 10 AFAU/g DS, preferably 0.10 to 5 AFAU/g DS, especially 0.3 to 2 AFAU/g DS.

Commercial Alpha-Amylase Products

Preferred commercial compositions comprising alpha-amylase include MYCOLASE from DSM, BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, and SPEZYME™ DELTA AA (Genencor Int.), and the acid fungal alpha-amylase sold under the trade name SP288 (available from Novozymes A/S, Denmark).

Carbohydrate-Source Generating Enzyme

The phrase "carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process for producing a fermentation product such as ethanol. The generated carbohydrate may be converted directly or indirectly to the desired fermentation product, preferably ethanol. According to the invention a mixture of carbohydrate-source generating enzymes may be present. Especially contemplated mixtures are mixtures of at least a glucoamylase and an alpha-amylase, especially an acid amylase, even more preferred an acid fungal alpha-amylase. The ratio between acidic fungal alpha-amylase activity (AFAU) per glucoamylase activity (AGU) (AFAU per AGU) may in an embodiment of the invention be at least 0.1, in particular at least 0.16, such as in the range from 0.12 to 0.50 or greater.

Glucoamylase

A glucoamylase used according to the invention may be derived from any suitable source, e.g., derived from a microorganism or a plant. Preferred glucoamylases are of fungal or bacterial origin selected from the group consisting of *Aspergillus* glucoamylases, in particular *A. niger* G1 or G2 glucoamylase (Boel et al., 1984, EMBO J. 3 (5), p. 1097-1102), and variants thereof, such as those disclosed in WO 1992/00381, WO 2000/04136 and WO 2001/04273 (from Novozymes, Denmark); the *A. awamori* glucoamylase disclosed in WO 1984/02921, *A. oryzae* glucoamylase (Agric.

Biol. Chem. 1991, 55 (4), p. 941-949), and variants or fragments thereof. Other *Aspergillus* glucoamylase variants include variants with enhanced thermal stability: G137A and G139A (Chen et al., 1996, Prot. Eng. 9, 499-505); D257E and D293E/Q (Chen et al., 1995, Prot. Eng. 8, 575-582); N182 (Chen at al., 1994, Biochem. J. 301, 275-281); disulphide bonds, A246C (Fierobe et al., 1996, Biochemistry, 35, 8698-8704; and introduction of Pro residues in position A435 and S436 (Li et al., 1997, Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al., 1998, Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 1999/28448), *Talaromyces leycettanus* (U.S. Pat. No. Re. 32,153), *Talaromyces duponti*, *Talaromyces thermophilus* (U.S. Pat. No. 4,587,215).

Bacterial glucoamylases contemplated include glucoamylases from the genus *Clostridium*, in particular *C. thermoamylolyticum* (EP 135,138), and *C. thermohydrosulfuricum* (WO 1986/01831) and *Trametes cingulata* disclosed in WO 2006/069289 (which is hereby incorporated by reference).

Hybrid glucoamylase are also contemplated according to the invention. Examples the hybrid glucoamylases are disclosed in WO 2005/045018. Specific examples include the hybrid glucoamylase disclosed in Table 1 and 4 of Example 1 of WO 2005/045018, which is hereby incorporated by reference to the extent it teaches hybrid glucoamylases.

Contemplated are also glucoamylases which exhibit a high identity to any of above mention glucoamylases, i.e., more than 70%, more than 75%, more than 80%, more than 85% more than 90%, more than 95%, more than 96%, more than 97%, more than 98%, more than 99% or even 100% identity to the mature enzymes sequences.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int): AMIGASE™ and AMIGASE™ PLUS (from DSM); G-ZYME™ G900, G-ZYMET™ and G990 ZR (from Genencor Int.).

Glucoamylases may in an embodiment be added in an amount of 0.02-20 AGU/g DS, preferably 0.1-10 AGU/g DS, especially between 1-5 AGU/g DS, such as 0.5 AGU/g DS.

Beta-Amylase

The term "beta-amylase" (E.C 32.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylase

The amylase may also be a maltogenic alpha-amylase. A maltogenic alpha-amylase (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Proteases

A protease may be added during hydrolysis in step ii), fermentation in step ill) or simultaneous hydrolysis and fermentation. The protease may be added to deflocculate the fermenting organism, especially yeast, during fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Especially contemplated are proteases derived from *Aspergillus niger* (see, e.g., Koaze et al. 1964, Agr. Biol. Chem. Japan, 28, 216), *Aspergillus saitoi* (see, e.g., Yoshida, 1954, J. Agr. Chem. Soc. Japan, 28, 66), *Aspergillus awamori* (Hayashida et al., 1977, Agric. Biol. Chem., 42(5), 927-933, *Aspergillus aculeatus* (WO 1995/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ ID NO:1 in WO 2003/048353 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.422.14 (actinidain), EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor miehei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Hand-book of Proteolytic Enzymes, Edited by A. J. Barrett, N. D. Rawlings and J. F. Woessner, Academic Press, San Diego, 1998, Chapter 270). Suitable examples of aspartic acid protease include, e.g., those disclosed in R. M. Berka et al., Gene, 96, 313 (1990)); (R. M. Berka et al., Gene, 125, 195-198 (1993)); and Gomi et al., Biosci. Biotech. Biochem. 57, 1095-1100 (1993), which are hereby incorporated by reference.

Commercially available products include ALCALASE®, ESPERASE™, FLAVOURZYME™, PROMIX™, NEUTRASE™, RENNILASE®, NOVOZYM™ FM 2.0L, and NOVOZYM™ 50006 (available from Novozymes A/S, Denmark) and GC106™ and SPEZYME™ FAN from Genencor Int., Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

The invention described and claimed herein is not to be limited in scope by the specific embodiments herein disclosed, since these embodiments are intended as illustrations of several aspects of the invention. Any equivalent embodiments are intended to be within the scope of this invention as well as combinations of one or more of the embodiments. Various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties. The present invention is further described by the following examples which should not be construed as limiting the scope of the invention.

Materials & Methods

Materials

Cellulase preparation A: Cellulolytic composition comprising a polypeptide having cellulolytic enhancing activity (GH61A) disclosed in WO 2005/074656; a beta-glucosidase (fusion protein disclosed in WO 2008/057637) and cellulolytic enzymes preparation derived from *Trichoderma reesei*. Cellulase preparation A is disclosed in co-pending application PCT/US2008/065417.

Yeast:

RED START™ available from Red Star/Lesaffre, USA.

RWB218 was received from Royal Nedalco/The Netherlands and is described in Kuyper et al., 2005, *FEMS Yeast Research* 5, p. 925-934.

Unwashed pre-treated corn stover (PCS): Acid-catalyzed, steam-exploded obtained from The National Renewable Energy Laboratory, Golden, Colo.

Methods

Determination of Identity

The relatedness between two amino acid sequences or between two nucleotide sequences is described by the parameter "identity".

The degree of identity between two amino acid sequences may be determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

The degree of identity between two nucleotide sequences may be determined by the Wilbur-Lipman method (Wilbur and Lipman, 1983, *Proceedings of the National Academy of Science USA* 80: 726-730) using the LASERGENE™ MEGALIGN™ software (DNASTAR, Inc. Madison, Wis.) with an identity table and the following multiple alignment parameters: Gap penalty of 10 and gap length penalty of 10. Pairwise alignment parameters are Ktuple=3, gap penalty=3, and windows=20.

Measurement of Cellulase Activity Using Filter Paper Assay (FPU Assay)

1. Source of Method 1.1 The method is disclosed in a document entitled "Measurement of Cellulase Activities" by Adney, B. and Baker, J., 1996, Laboratory Analytical Procedure, LAP-006, National Renewable Energy Laboratory (NREL). It is based on the IUPAC method for measuring cellulase activity (Ghose, T. K., Measurement of Cellulse Activities, Pure & Appl. Chem. 59, pp. 257-268, 1987.

2. Procedure 2.1 The method is carried out as described by Adney and Baker, 1996, supra, except for the use of a 96 well plates to read the absorbance values after color development, as described below.

2.2 Enzyme Assay Tubes:

2.2.1 A rolled filter paper strip (#1 Whatman; 1×6 cm; 50 mg) is added to the bottom of a test tube (13×100 mm).

2.2.2 To the tube is added 1.0 mL of 0.05 M Na-citrate buffer (pH 4.80).

2.2.3 The tubes containing filter paper and buffer are incubated 5 min. at 50° C. (t 0.1° C.) in a circulating water bath.

2.2.4 Following incubation, 0.5 mL of enzyme dilution in citrate buffer is added to the tube. Enzyme dilutions are designed to produce values slightly above and below the target value of 2.0 mg glucose.

2.2.5 The tube contents are mixed by gently vortexing for 3 seconds.

2.2.6 After vortexing, the tubes are incubated for 60 mins. at 50° C. (±0.1° C.) in a circulating water bath.

2.2.7 Immediately following the 60 min. incubation, the tubes are removed from the water bath, and 3.0 mL of DNS reagent is added to each tube to stop the reaction. The tubes are vortexed 3 seconds to mix.

2.3 Blank and Controls 2.3.1 A reagent blank is prepared by adding 1.5 mL of citrate buffer to a test tube.

2.3.2 A substrate control is prepared by placing a rolled filter paper strip into the bottom of a test tube, and adding 1.5 mL of citrate buffer.

2.3.3 Enzyme controls are prepared for each enzyme dilution by mixing 1.0 mL of citrate buffer with 0.5 mL of the appropriate enzyme dilution.

2.3.4 The reagent blank, substrate control, and enzyme controls are assayed in the same manner as the enzyme assay tubes, and done along with them.

2.4 Glucose Standards 2.4.1 A 100 mL stock solution of glucose (10.0 mg/mL) is prepared, and 5 mL aliquots are frozen. Prior to use, aliquots are thawed and vortexed to mix.

2.4.2 Dilutions of the stock solution are made in citrate buffer as follows:

G1=1.0 mL stock+0.5 mL buffer=6.7 mg/mL=3.3 mg/0.5 mL

G2=0.75 mL stock+0.75 mL buffer=5.0 mg/mL=2.5 mg/0.5 ml.

G3=0.5 mL stock+1.0 mL buffer=3.3 mg/mL=1.7 mg/0.5 mL

G4=0.2 mL stock+0.8 mL buffer=2.0 mg/mL=1.0 mg/0.5 mL 2.4.3 Glucose standard tubes are prepared by adding 0.5 mL of each dilution to 1.0 mL of citrate buffer.

2.4.4 The glucose standard tubes are assayed in the same manner as the enzyme assay tubes, and done along with them.

2.5 Color Development 2.5.1 Following the 60 min. incubation and addition of DNS, the tubes are all boiled together for 5 mins. in a water bath.

2.5.2 After boiling, they are immediately cooled in an ice/water bath.

2.5.3 When cool, the tubes are briefly vortexed, and the pulp is allowed to settle. Then each tube is diluted by adding 50 microL from the tube to 200 microL of ddH2O in a 96-well plate. Each well is mixed, and the absorbance is read at 540 nm.

2.6 Calculations (Examples are Given in the NREL Document)

2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.

2.6.2 A plot of glucose produced (mg/0.5 mL) vs. total enzyme dilution is prepared, with the Y-axis (enzyme dilution) being on a log scale.

2.6.3 A line is drawn between the enzyme dilution that produced just above 2.0 mg glucose and the dilution that produced just below that. From this line, it is determined the enzyme dilution that would have produced exactly 2.0 mg of glucose.

2.6.4 The Filter Paper Units/mL (FPU/mL) are calculated as follows:

FPU/mL=0.37/enzyme dilution producing 2.0 mg glucose

Glucoamylase Activity

Glucoamylase activity may be measured in AGI units or in Glucoamylase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:

| | |
|---|---|
| Substrate: | Soluble starch, concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucase. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S. Denmark, which folder is hereby included by reference.

Alpha-Amylase Activity

Alpha-Amylase Activity (KNU)

The alpha-amylase activity may be determined using potato starch as substrate. This method is based on the breakdown of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

| Substrate: | Soluble starch. Concentration approx. 20 g DS/L. |
|---|---|
| Buffer: | Citrate, approx. 0.13 M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as calorimetric indicator. Lintner starch is obtained by dilute hydrochloric acid treatment of native starch so that it retains the ability to color blue with iodine. Further details can be found in EP 0140410 B2, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

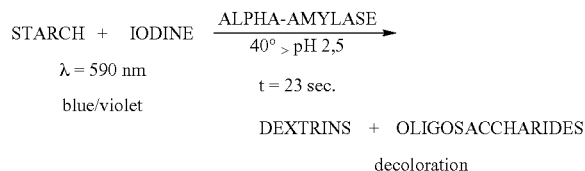

Standard Conditions/Reaction Conditions:

| Substrate: | Soluble starch, approx. 0.17 g/L |
|---|---|
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Xylose/Glucose Isomerase Assay (IGIU)

1 IGIU is the amount of enzyme which converts glucose to fructose at an initial rate of 1 micromole per minute at standard analytical conditions.

Standard Conditions:

| Glucose concentration: | 45% w/w |
|---|---|
| pH: | 7.5 |
| Temperature: | 60° C. |
| Mg2+ concentration: | 99 mg/l (1.0 g/l MgSO4 * 7 $H_2O$) |
| Ca2+ concentration | <2 ppm |
| Activator, $SO_2$ concentration: | 100 ppm (0.18 g/l $Na_2S_2O_5$) |
| Buffer, $Na_2CO_3$, concentration: | 2 mM $Na_2CO_3$ |

Protease Activity
Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of ICA soluble product is determined with phenol reagent, which gives a blue color with tyrosine and tryptophan.

One Anson Unit (AU(RH)) is defined as the amount of enzyme which under standard conditions (i.e., 25° C., pH 5.5 and 10 min. reaction time) digests hemoglobin at an initial rate such that there is liberated per minute an amount of TCA soluble product which gives the same color with phenol reagent as one milliequivalent of tyrosine.

AU(RH) is described in EAL-SM-0350 available from Novozymes A/S Denmark on request.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

Measurement of Yeast Dry Weight

Dry weight of RED STAR™ was determined by directly weighing the dry yeast cell granules. Dry weight of the RWB218 was determined by optical density (OD) measurement of the cells by spectrophotometer at 600 nm, using the pre-determined correlation of the OD and the dry cell weight. An OD of 1 correlates to 0.26 g/L of dry cells.

EXAMPLES

Example 1

High Cell Count Ethanol Production

The effect of high yeast pitch (cell count) and cell recycling on ethanol production was tested by inoculating filtered, pretreated corn stover (PCS) enzyme hydrolyzate at various initial yeast cell concentrations. At 24 and 48 hours after the start of the fermentation, cells were recycled by centrifugation, spent hydrolyzate was removed and fresh hydrolyzate was added.

Method:

Unwashed PCS (acid-catalyzed, steam-exploded, The National Renewable Energy Laboratory, Golden, Colo.), was hydrolyzed for 72 hours at 50° C. using an initial insoluble solids concentration of 20% (w/w) and 10 mg of Cellulase preparation A per g of cellulose. After hydrolysis, the slurry was centrifuged for 10 minutes at 3000 rpm, and the supernatant was collected by filtration using a 0.45 micron Whatman filter.

Into the wells of a 24-well cell culture plate (Whatman International Ltd., Florham Park, N.J.) varying amounts of RED STAR™ yeast were added ranging from 1 g dry cells/L to 50 g dry cells/L. To each well, 4 mL of PCS enzymatic hydrolyzate, pH 5.0 were added, and the cells were re-suspended with mild agitation. The plate was sealed and incubated in a dry air incubator at 32° C. with shaking at 150 rpm. Samples were collected at 0, 4, 8, and 24 hours for ethanol determination. An enzyme-coupled microtiter plate assay was utilized for ethanol quantitation (reagents from Diagnostic Chemicals Ltd., Prince Edward Island, Canada). After 24 hours, the cells were collected by centrifugation at 3000 rpm for 12 minutes, and the supernatants were discarded. Next, 4 mL of fresh PCS hydrolyzate were added to each well, and the yeast cells were re-suspended with a glass stirring rod. Samples were collected immediately and following a second 24 hours incubation at 32° C., after which time the fermentation plate was re-centrifuged and supernatants discarded. Four mL of fresh PCS hydrolyzate were again added to each well, and the cells were re-suspended. Samples were collected immediately and at 4, 8, and 24 hours during the third day of fermentation. The fermentation was ended 72 hours after initiation and each well was sampled for standard HPLC analyses.

TABLE 1

Ethanol concentrations (g/L) over time as a function of yeast cell pitch and cell recycle.

| Time, hrs | Yeast pitch, g dry cells/L | | | | | | |
|---|---|---|---|---|---|---|---|
| | 1 | 5 | 10 | 20 | 30 | 40 | 50 |
| 0 | 1.8 | 1.8 | 1.8 | 1.8 | 1.8 | 1.8 | 1.8 |
| 4 | 1.7 | 3.6 | 9.0 | 18.1 | 29.3 | 35.5 | 33.8 |
| 8 | 1.7 | 8.0 | 14.1 | 34.6 | 35.8 | 40.9 | 41.9 |
| 24 | 1.3 | 18.8 | 30.6 | 31.7 | 32.7 | 35.3 | 38.0 |
| 25 | 1.2 | 1.9 | 2.5 | 3.8 | 4.9 | 5.5 | 7.0 |
| 48 | 5.4 | 18.1 | 25.2 | 31.2 | 34.5 | 31.7 | 34.1 |
| 49 | 2.1 | 1.9 | 2.2 | 3.0 | 4.0 | 4.8 | 5.8 |
| 53 | 5.9 | 6.6 | 7.4 | 12.1 | 16.4 | 19.2 | 22.4 |
| 57 | 6.6 | 12.1 | 11.7 | 18.1 | 24.6 | 27.2 | 32.0 |
| 72 | 36.4 | 37.0 | 30.4 | 43.6 | 35.4 | 34.7 | 38.6 |

Example 2

Low Cell Count Ethanol Production

The effect of various amounts of sugar solutions and filtered, pre-treated corn stover (PCS) enzyme hydrolyzate on batch fermentation ethanol production in different yeast strains was tested. The results are summarized in FIG. 1.

Method:

Ten different media were batch fermented to produce ethanol by RED STAR™ yeast and RWB218 (Nedalco). Mediums 1 to 5 were glucose and xylose solutions supplemented with 0.5% (w/v) yeast extract and 1% (w/v) peptone. Mediums 6 to 10 were filtered unwashed pretreated corn stover (fuwPCS) enzyme hydrolyzate with different levels of total solids. Sugar level of Mediums 5 to 9 was adjusted to make xylose and glucose concentration equivalent to that found in 20% total solids of fuwPCS hydrolyzate to test the resistance of the strains towards different level of inhibitions. All media were filter sterilized.

Medium 1: Xylose only at 40 g/L
Medium 2: Glucose only at 40 g/L
Medium 3: Xylose 20 g/L and Glucose 20 g/L (low dose)
Medium 4: Xylose 60 g/L and Glucose 80 g/L (high dose)
Medium 5: 0% TS of fuwPCS in Xylose 40 g/L and Glucose 75 g/L
Medium 6: 1% TS of fuwPCS in Xylose 40 g/L and Glucose 75 g/L
Medium 7: 5% TS of fuwPCS in Xylose 40 g/L and Glucose 75 g/L
Medium 8: 10% TS of fuwPCS in Xylose 40 g/L and Glucose 75 g/L
Medium 9: 15% TS of fuwPCS in Xylose 40 g/L and Glucose 75 g/L
Medium 10: 20% TS of fuwPCS in Xylose 40 g/L and Glucose 75 g/L Unwashed PCS (acid-catalyzed, steam-exploded, The National Renewable Energy Laboratory, Golden, Colo.) was diluted with water and adjusted to pH 5.0 with NaOH. Penicillin, citrate buffer and YP medium (0.5% (w/v) yeast extract and 1% (w/v) peptone) were also added prior to hydrolysis. The sample was hydrolyzed for 96 hours at 50° C. with Cellulase preparation A at total solids concentration of 20% (w/w). After hydrolysis, the slurry was centrifuged for 10 minutes at 3000 rpm, and the supernatant, pH 5.0, was collected by sterile-filtration and used for fermentation.

Fermentations were carried on in autoclaved 20 ml mini vials at 30° C. for 96 hrs. Both yeasts were tested in ten fermentation media as listed above. All tests were conducted in triplicate. The pre-culture was inoculated into 5 ml fermentation media contained in 20 ml mini vial with initial cell density around 0.25 g/L. The mini vials were then incubated in the shaker at 150 rpm for four days. Samples were taken at the end of fermentation to measure the ethanol, glucose, xylose, acetic acid and glycerol levels by HPLC. The HPLC preparation consisted of stopping the reaction by addition of 40% $H_2SO_4$ (1% v/v addition), centrifuging, and filtering through a 0.20 micrometer filter. Samples were stored at 4° C. until analysis. Agilent™ 1100 HPLC system coupled with RI detector was used. The separation column was aminex HPX-87H ion exclusion column (300 mm×7.8 mm) from Bio-Rad™.

Example 3

High Cell Count Ethanol Production

Figure 2:
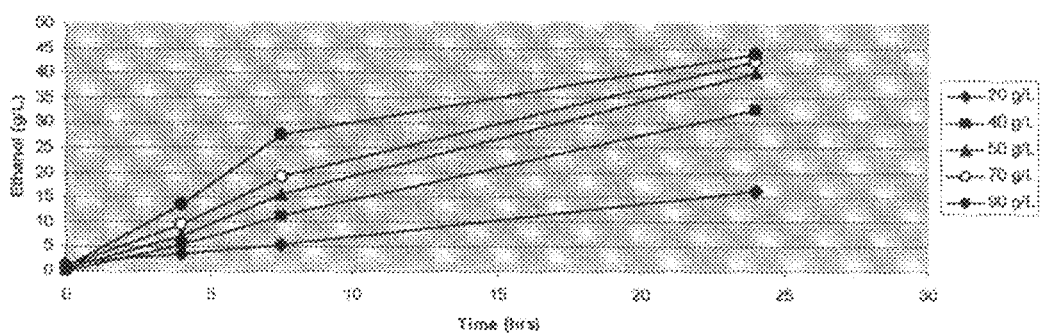
FIG. 2 demonstrates the effect of high cell density of RED STAR™ on ethanol batch fermentation of filtered, pre-treated corn stover (PCS) enzyme hydrolyzate at various initial yeast cell concentrations.

The effect of high RED START™ yeast pitch (cell count) on batch fermentation ethanol production was tested by inoculating filtered, pre-treated corn stover (PCS) enzyme hydrolyzate at various initial yeast cell concentrations. The results are summarized in FIG. 2.

Method:

Unwashed PCS (acid-catalyzed, pretreated corn stover from National Renewable Energy Laboratory, Golden, Colo.), was hydrolyzed for 120 hours at 50° C., pH 5.0 using an initial solids concentration of 20% (w/w) and 50 mg of Cellulase preparation A per g of cellulose. After hydrolysis, the slurry was centrifuged for 10 minutes at 3000 rpm using a Beckman-Coulter table top centrifuge to separate the solids.

The resulting liquid hydrolyzate was supplemented with nutrients: yeast extract and peptone at 5 g/L levels each and fermented using a shaker incubator at 150 rpm for 24 hrs at a temperature of 32° C. and pH 5.0 in a 250 mL nalgene bottle with a 150 mL working volume by varying the initial yeast cell concentration of red star dry yeast from 20 g/L to 90 g/L. Samples were collected at 3, 7 and 24 hrs and analyzed for glucose consumption and ethanol production using a HPLC.

Example 4

High Cell Count Ethanol Production

Figure 3:
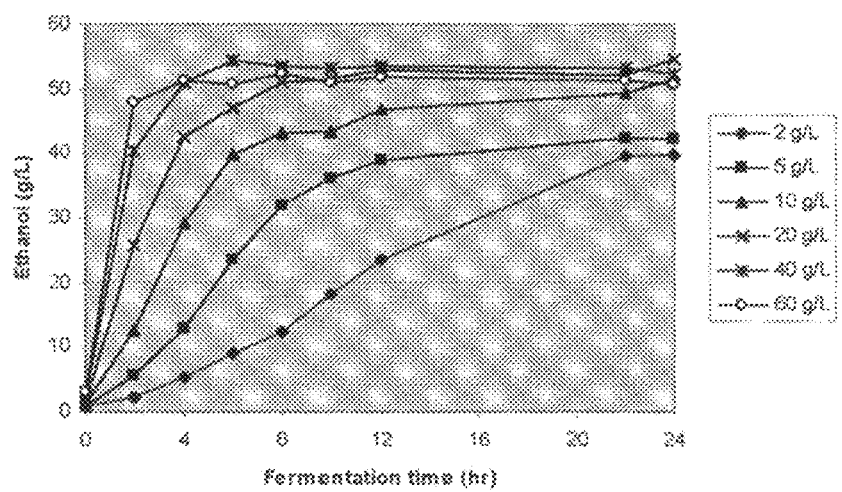
FIG. 3 demonstrates the effect of high cell density of yeast RWB218 on ethanol batch fermentation of pre-treated corn stover (PCS) enzyme hydrolyzate at various initial yeast cell concentrations.

The effect of high RWB218 yeast pitch (cell count) on batch fermentation ethanol production was tested by inoculating pre-treated corn stover (PCS) enzyme hydrolyzate at various initial yeast cell concentrations. The results are summarized in FIG. 3.

Method:

Unwashed PCS (acid-catalyzed, steam-exploded, The National Renewable Energy Laboratory, Golden, Colo.) was diluted with water and adjusted to pH 5.0 with NaOH. Penicillin and citrate buffer were also added prior to hydrolysis. The sample was hydrolyzed for 96 hours at 50° C. with Cellulase preparation A at a total solids concentration of 23% (w/w). After hydrolysis, the slurry was centrifuged for 15 minutes at 3000 rpm, and the supernatant was collected. Prior to fermentation, the supernatant was supplemented with 0.5% yeast extract (w/v) and 0.5% (w/v) peptone, and adjusted pH to 6.0 with $NH_4OH$. Certain amount of water was added to make the final total solids concentration of the hydrolyzate to 20% (w/w).

Fermentations were carried on in 125 ml flasks at 30° C. Each flask contained 50 ml of the above hydrolyzate liquid and was inoculated with RWB218 at initial cell density of 2, 5, 10, 20, 40 and 60 g cells per liter. The flasks were incubated in the shaker at 150 rpm for 24 hours. Samples were taken at 0, 2, 4, 6, 8, 10, 12, 22, and 24 hours of the fermentation to measure the ethanol, glucose, xylose, acetic acid and glycerol levels by HPLC. The HPLC preparation consisted of stopping the reaction by addition of 40% $H_2SO_4$ (1% v/v addition), centrifuging, and filtering through a 0.20 micrometer filter. Samples were stored at 4° C. until analysis. Agilent™ 1100 HPLC system coupled with R1 detector was used. The separation column was aminex HPX-87H ion exclusion column (300 mm×7.8 mm) from BioRad™.

Example 5

Recycled High Cell Count Ethanol Production

Figure 4:
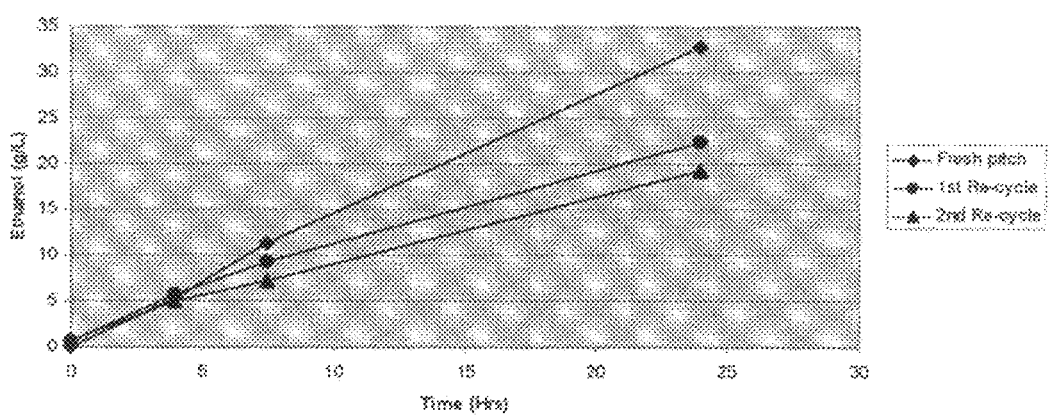
FIG. 4 demonstrates the effect of high cell density of RED STAR™ and cell recycling at pH5 on batch fermentation ethanol production of filtered, pre-treated corn stover (PCS) enzyme hydrolyzate at an initial yeast cell concentration of 40 g/L.

The effect of high RED START™ yeast pitch (cell count) and cell recycling at pH5 on batch fermentation ethanol production was tested by inoculating filtered, pre-treated corn stover (PCS) enzyme hydrolyzate at an initial yeast cell concentration of 40 g/L. At 24 and 48 hours after the start of the fermentation, cells were recycled by centrifugation, spent hydrolyzate was removed and fresh hydrolyzate was added. The results are summarized in FIG. 4.

Method:

Unwashed PCS (acid-catalyzed, pretreated corn stover from National Renewable Energy Laboratory, Golden, Colo.), was hydrolyzed for 120 hours at 50° C., pH 5.0 using an initial solids concentration of 20% (w/w) and 50 mg of Cellulase preparation A per g of cellulose. After hydrolysis, the slurry was centrifuged for 10 minutes at 3000 rpm using a Beckman-Coulter table top centrifuge to separate the solids. The resulting liquid hydrolyzate was supplemented with nutrients: yeast extract and peptone at 5 g/L levels each, and fermented using a shaker incubator at 150 rpm for 24 hrs at a temperature of 32° C. and pH 5.0 in a 250 mL nalgene bottle with a 150 mL working volume at an initial yeast cell concentration of 40 g/L. Every 24 hrs, the nalgene bottle containing the liquid hydrolyzate and the yeast cells was centrifuged at 3000 rpm for 10 min using a Beckman-Coulter table top centrifuge. Fermented liquid hydrolyzate containing ethanol was decanted and the fresh hydrolyzate containing nutrients was added (150 mL volume) and the yeast cells were re-suspended in the same nalgene bottle and re-incubated at 32 C and 150 rpm in a shaker incubator as before. Samples were collected at 3, 7 and 23.5 hrs for each fermentation cycle and analyzed for glucose consumption and ethanol production using HPLC.

Example 6

Recycled High Cell Count Ethanol Production

Figure 5:
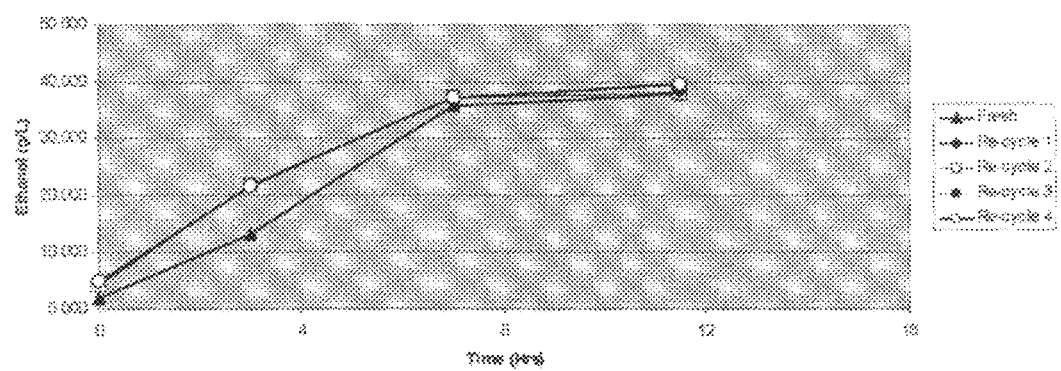
FIG. 5 demonstrates the effect of high cell density of RED STAR™ and cell recycling at pH 6 on batch fermentation ethanol production of filtered, pre-treated corn stover (PCS) enzyme hydrolyzate at an initial yeast cell concentration of 40 g/L.

The effect of high RED STAR™ yeast pitch (cell count) and cell recycling at pH6 on batch fermentation ethanol production was tested by inoculating filtered, pre-treated corn stover (PCS) enzyme hydrolyzate at an initial yeast cell concentration of 40 g/L. At 12 hours after the start of each fermentation cycle, cells were recovered by centrifugation, spent hydrolyzate was removed and fresh hydrolyzate was added. The results are summarized in FIG. 5.

Method:

Unwashed PCS (acid-catalyzed, pretreated corn stover from National Renewable Energy Laboratory, Golden, Colo.), was hydrolyzed for 120 hours at 50° C., pH 5.0 using an initial solids concentration of 20% (w/w) and 50 mg of Cellulase preparation A per g of cellulose. After hydrolysis, the slurry was centrifuged for 10 minutes at 3000 rpm using a Beckman-Coulter table top centrifuge. The resulting liquid hydrolyzate was supplemented with nutrients: yeast extract and peptone at 5 g/L levels each, and fermented using a shaker incubator at 150 rpm for 12 hrs at a temperature of 32° C. and pH 6.0 in a 250 mL nalgene bottle with a 150 mL working volume at an initial yeast cell concentration of 40 g/L. 10% (w/w) sodium hydroxide solution was used for adjusting the pH to 6.0. Every 12 hrs, the nalgene bottle containing the liquid hydrolyzate and the yeast cells was centrifuged at 3000 rpm for 10 min using a Beckman-Coulter table top centrifuge. Fermented liquid hydrolyzate containing ethanol was decanted and the fresh hydrolyzate containing nutrients was added (150 mL volume) and the yeast cells were re-suspended in the same nalgene bottle and re-incubated at 32° C. and 150 rpm in a shaker incubator as before. Samples were collected at 3, 7 and 11.5 hrs after the start of each fermentation cycle and analyzed for glucose consumption and ethanol production using a HPLC. The same experiments were conducted at 15% (w/w) initial solids concentration in media supplemented with approximately 20 g/L glucose. Cells were recycled eight (8) times for a total of nine (9) fermentation cycles. Each fermentation cycle produced approximately 37 g/L ethanol, indicating no loss in the fermentation productivity of the recycled yeast even after 9 fermentation cycles. (Data not shown).

Example 7

Recycled High Cell Count Ethanol Production

Figure 6A:
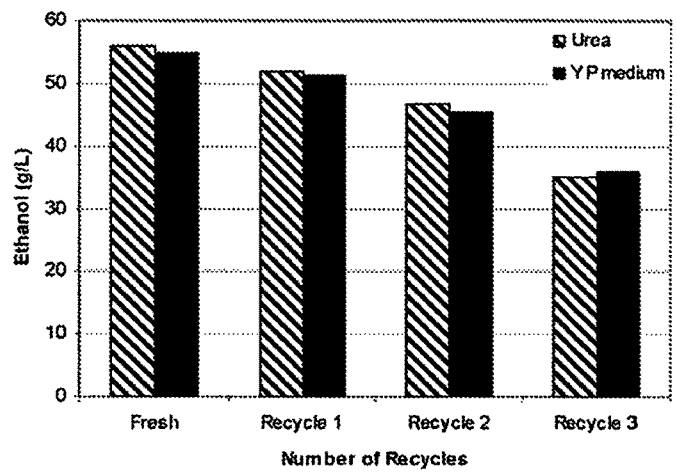
FIG. 6a demonstrates the effect of high cell density of yeast RWB218 and cell recycling on fed-batch fermentation ethanol production of centrifuged, pre-treated corn stover (PCS) enzyme hydrolyzate at a yeast cell concentration of 20 g/L.
Figure 6B:
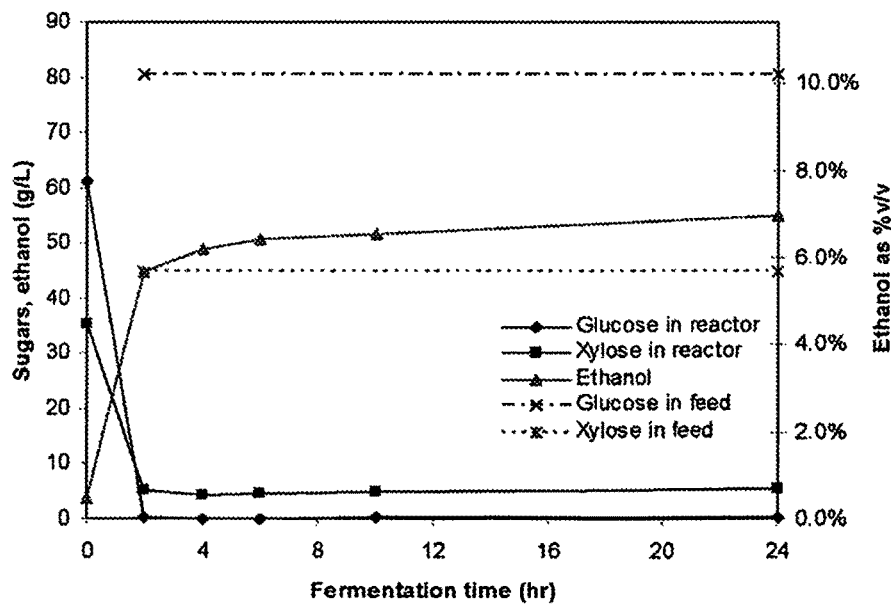
FIG. 6b demonstrates the effect of high cell density of yeast RWB218 on fed-batch fermentation ethanol production of centrifuged, pre-treated corn stover (PCS) enzyme hydrolyzate at a yeast cell concentration of 20 g/L from 0 to 24 hours.

The effect of high RWB218 yeast pitch (cell count) and cell recycling on fed-batch fermentation ethanol production was tested by inoculating centrifuged, pre-treated corn stover (PCS) enzyme hydrolyzate at a yeast cell concentration of 20 g/L. At 24 hours after the start of the each fermentation, cells were recycled by centrifugation, spent hydrolyzate was removed and fresh hydrolyzate was added. The results for each fermentation cycle are shown in FIG. 6a, and details of the first fermentation cycle are shown in FIG. 6b.

Method:

Unwashed PCS (acid-catalyzed, steam-exploded, The National Renewable Energy Laboratory, Golden, Colo.) was diluted with water and adjusted to pH 5.0 with NaOH. Penicillin and citrate buffer were also added prior to hydrolysis. The sample was hydrolyzed for 96 hours at 50° C. with Cellulase preparation A at total solids concentration of 23% (w/w). After hydrolysis, the slurry was centrifuged for 15 minutes at 3000 rpm, and the supernatant was collected. Prior to fermentation, the supernatant was supplemented with 0.5% (w/v) yeast extract and 0.5% (w/v) peptone, or 0.1% (w/v) urea, and adjusted pH to 6.0 with $NH_4OH$. Water was added to make the final total solids concentration of the hydrolyzate 20% (w/w).

Fermentations were carried out in 250 ml Nalgene bottles at 30° C. One bottle initially contained 40 ml of the above hydrolyzate liquid supplemented with yeast extract and peptone, and the other bottle contained 40 ml of the above hydrolyzate liquid supplemented with urea. Both bottles were inoculated with RWB218 at a cell density of 20 g cells per liter (based on the total working volume of 200 ml). The bottles were then incubated in the shaker at 150 rpm. Feeding of the same hydrolyzate liquid as batch was started after two hours of fermentation. The total feed volume was 160 ml and total feed time was between 22 and 40 hrs. After the feed was completed, the Nalgene bottle containing the fermentation beer and the yeast cells was centrifuged at 3000 rpm for 15 minutes. 160 ml of the supernatant containing ethanol was decanted and the remaining 40 ml left in the bottle was mixed well with the yeast cells. The bottle was re-incubated in the shaker at 30° C. and 150 rpm as before, and feed was re-initiated with the feed bottle refilled with another 160 ml of same hydrolyzate liquid as before. Samples were collected during each cycle of the fermentation to measure the ethanol, glucose, xylose, acetic acid and glycerol levels by HPLC. The HPLC preparation consisted of stopping the reaction by addition of 40% $H_2SO_4$ (1% v/v addition), centrifuging, and filtering through a 0.20 micrometer filter. Samples were stored at 4° C. until analysis. Agilent™ 1100 HPLC system coupled with R1 detector was used. The separation column was aminex HPX-87H ion exclusion column (300 mm×7.8 mm) from BioRad™.

Example 8

High Cell Count Ethanol Production

Figure 7:
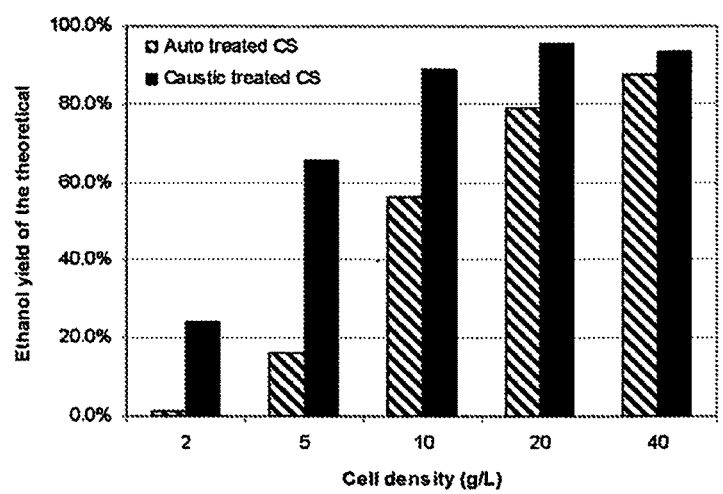
FIG. 7 demonstrates the effect of high density of yeast RWB218 on batch fermentation ethanol production from corn stover (CS) pre-treated with various pre-treatment methods on pre-treated corn stover (PCS) enzyme hydrolyzate at various initial yeast cell concentrations.

The effect of high RWB218 yeast pitch (cell count) on batch fermentation ethanol production from corn stover (CS) pre-treated with various pre-treatment methods was tested by inoculating pre-treated corn stover (PCS) enzyme hydrolyzate at various initial yeast cell concentrations. The results are summarized in FIG. 7.

Method:

Unwashed auto-pretreated corn stover, and unwashed caustic-pretreated corn stover (The National Renewable Energy Laboratory, Golden, Colo.), were diluted with water and adjusted to pH 5.0 with either NaOH or $H_2SO_4$ respectively. Penicillin and citrate buffer were also added prior to hydrolysis. The samples were hydrolyzed for 48 hours at 50° C. with Cellulase preparation A and SHEARSYME™ at total solids concentration of 20% (w/v). After hydrolysis, the slurry was centrifuged for 15 minutes at 3000 rpm, and the supernatant was collected. Prior to fermentation, the supernatant was supplemented with 0.5% (w/v) yeast extract and 0.5% (w/v) peptone.

Fermentations were carried out in 125 ml flasks at 30° C. Each flask contained 50 ml of the above hydrolyzate liquids and inoculated with RWB218 at initial cell density of 2, 5, 10, 20 and 40 g cells per liter. The flasks were incubated in the shaker at 150 rpm for 24 hours. Samples were taken at 0, 2, 4, 6, 20 and 24 hours of the fermentation to measure the ethanol, glucose, xylose, acetic acid and glycerol levels by HPLC. The HPLC preparation consisted of stopping the reaction by addition of 40% $H_2SO_4$ (1% v/v addition), centrifuging, and filtering through a 0.20 micrometer filter. Samples were stored at 4° C. until analysis. Agilent™ 1100 HPLC system coupled with R1 detector was used. The separation column was aminex HPX-87H ion exclusion column (300 mm×7.8 mm) from BioRad™.

The invention claimed is:

1. A method for producing ethanol, comprising:
    i) pre-treating a lignocellulose-containing material;
    ii) hydrolyzing the pre-treated lignocellulose-containing material;
    iii) fermenting using a yeast;
    iv) recovering the ethanol after fermentation;
wherein the hydrolysis and fermentation steps are carried out as a separate hydrolysis and fermentation; the fermentation is initiated and carried out at a yeast concentration of 10-50 g dry weight yeast per L fermentation medium; and the fermentation is carried out as fed-batch fermentation where C6 and C5 sugars are fermented simultaneously, and wherein the yeast is of the genus *Saccharomyces*.

2. The method of claim 1, wherein in-soluble solids are removed before or during fermentation.

3. The method of claim 1, wherein in-soluble solids are removed after pre-treating the lignocellulose-containing material in step i).

4. The method of claim 2, wherein in-soluble solids are removed after hydrolyzing the pre-treated lignocellulose-containing material in step ii).

5. The method of claim 1, wherein yeast are recovered after fermentation and re-used.

6. The method of claim 1, wherein xylose isomerase is used during hydrolysis.

7. The method of claim 1, wherein the lignocellulose-containing material is detoxified before fermentation or hydrolysis.

8. The method of claim 1, wherein the lignocellulose-containing material introduced into the fermentation medium is un-washed.

9. The method of claim 1, wherein pre-treatment is carried out as a dilute acid steam explosion step.

10. The method of claim 1, wherein the lignocellulose-containing material is derived from corn stover, corn fiber, hard wood, soft wood, cereal straw, switch grass, Miscanthus, rice hulls, municipal solid waste, industrial organic waste, office paper, or mixtures thereof.

11. The method of claim 1, wherein the lignocellulose-containing material is hydrolyzed by treatment with one or more cellulase or hemicellulase enzymes, or combinations thereof.

12. The method of claim 11, wherein the cellulase used for hydrolysis is a cellulolytic preparation derived from a strain of *Trichoderma*.

13. The method of claim 12, wherein the strain of *Trichoderma* is a strain of *Trichoderma reesei*.

14. The method of claim 11, further wherein one or more polypeptides having cellulolytic enhancing activity is present during hydrolysis.

15. The method of claim 1, wherein the pH during fermentation is between 3 and 7.

16. The method of claim 1, wherein the fermentation is carried out for 1-48 hours.

17. A method for producing ethanol, comprising:
   i) pre-treating a lignocellulose-containing material;
   ii) hydrolyzing the pre-treated lignocellulose-containing material;
   iii) fermenting using a yeast;
   iv) recovering the ethanol after fermentation; and
   v) recovering yeast for use in one or more additional fermentation cycles, wherein the hydrolysis and fermentation steps are carried out as a separate hydrolysis and fermentation; the fermentation is initiated and carried out at a yeast concentration of 10-50 g dry weight yeast per L fermentation medium; the fermentation is carried out as fed-batch fermentation where C6 and C5 sugars are fermented simultaneously; steps iii-v are repeated at least one time, wherein the recovered yeast of step v is recycled into fermenting step iii, and wherein the yeast is of the genus *Saccharomyces*.

18. The method of claim 1, wherein the yeast is *Saccharomyces cerevisiae* or *Saccharomyces uvarum*.

19. The method of claim 17, wherein the yeast is *Saccharomyces cerevisiae* or *Saccharomyces uvarum*.

* * * * *